United States Patent [19]

Oka et al.

[11] Patent Number: 5,157,454
[45] Date of Patent: Oct. 20, 1992

[54] DIFFERENTIAL REFRACTOMETER

[75] Inventors: Koichi Oka, Shiga; Akira Kawaguchi, Kyoto; Kunio Kumagai; Yasuhiro Kubo, both of Shiga, all of Japan

[73] Assignee: Otsuka Electronics Co., Ltd., Osaka, Japan

[21] Appl. No.: 618,430

[22] Filed: Nov. 27, 1990

[30] Foreign Application Priority Data

Nov. 30, 1989 [JP] Japan ................... 1-311473

[51] Int. Cl.$^5$ .............................................. G01N 21/41
[52] U.S. Cl. ....................................... 356/130; 356/134
[58] Field of Search ............... 356/128, 130, 131, 132, 356/134

[56] References Cited

U.S. PATENT DOCUMENTS

| 454,989 | 6/1891 | Sonden | 356/130 |
|---|---|---|---|
| 2,810,315 | 10/1957 | Miller | 356/132 |
| 3,386,332 | 6/1968 | Watson | 356/130 |
| 3,539,263 | 11/1970 | Waters | 356/131 |
| 3,674,373 | 7/1972 | Waters | 356/130 |

FOREIGN PATENT DOCUMENTS

| 35195 | 10/1956 | Fed. Rep. of Germany | 356/130 |
|---|---|---|---|
| 63-188744 | 8/1988 | Japan . | |
| 63-295935 | 12/1988 | Japan . | |
| 593122 | 2/1978 | U.S.S.R. | 356/128 |
| 641333 | 1/1979 | U.S.S.R. | 356/130 |
| 942094 | 11/1963 | United Kingdom | 356/130 |
| 1097526 | 1/1968 | United Kingdom . | |

*Primary Examiner*—Richard A. Rosenberger
*Attorney, Agent, or Firm*—Sughrue, Mion, Zinn, Macpeak & Seas

[57] ABSTRACT

A differential refractometer in which: light from a light source is condensed on a lens; the light thus condensed is guided to a cell which houses a sample of which refractive index is to be measured and a reference of which refractive index is used as a reference value, the sample and the reference being housed as separated from each other in the cell; the light having passed through the cell is guided to an image sensor; and the amount of light deflection due to the difference in refractive index between the sample and the reference is measured, thereby to obtain the refractive index of the sample. The differential refractometer comprises: a light permeable member disposed at such a position that the light permeable member and the image sensor are optically conjugate with respect to the lens, the light permeable member carrying an image having at least two identification portions; and a spatial filter disposed between the light permeable member and the image sensor and adapted to spatially filter light portions which have passed through the two identification portions, the spatial filter causing at least one of the light portions thus spatially filtered to pass through the cell. The refractive index of the sample may be obtained based on the distance between the positions of images, on the detecting surface of the image sensor, of the two identification portions of the light permeable member. Such an arrangement may improve the measuring precision and reduce the number of component elements.

15 Claims, 7 Drawing Sheets

DIFFERENTIAL REFRACTOMETER

BACKGROUND OF THE INVENTION

The present invention relates to a differential refractometer to be used for determining a molecular weight for example.

There is known a technique for measuring the refractive index of a solution and the dependency thereof on the concentration to measure the molecular weight of a sample which is a solute of the solution. The refractive index of a sample solution may be measured, for example, with the use of a cell having a transparent container in which the sample solution and its solvent are housed as separated from each other. When monochromatic light is incident upon the cell through a slit, the optical path of the incident light is deflected according to the difference in refractive index between the sample solution and the solvent. Accordingly, when the refractive index of the solvent is known, the refractive index of the sample solution may be obtained. Thus, it is a differential refractometer that is adapted to measure the refractive index of a sample with the use of the fact that the incident light is deflected according to the difference in refractive index between a reference of which refractive index is known (the solvent of the sample solution in the example above-mentioned) and a sample of which refractive index is unknown (the sample solution).

The basic arrangement of a conventional differential refractometer is shown in FIG. 21. Light from a light source 1 is guided, through a slit plate 2, to a collimater lens 3 where the light is collimated. The parallel light portions are incident upon a cell 5, as a light flux A of which width is restricted by a slit plate 4. The light flux A from the cell 5 passes through an image forming lens 6 and a correction glass plate 7 to be discussed later, and forms a slit image formed by the slit plate 4 on a detecting surface of a photosensor 8 disposed at the side of the focal surface of the image forming lens 6. The correction glass plate 7 may be angularly displaced in a direction shown by an arrow R1 by operating a dial 9.

FIG. 22 is an enlarged transverse section view of the cell 5 showing the arrangement thereof. This cell 5 is called a Brice cell or the like in which a cell container 5a is formed by a transparent casing body having a rectangular section and in which the inside space of the cell container 5a is obliquely partitioned by a partitioning plate 5b to form a first chamber 51 and a second chamber 52. For example, when the first chamber 51 is filled with a sample solution of which refractive index is to be measured, and the second chamber 52 is filled with a solvent for the sample solution, the light flux A from the slit plate 4 is deflected according to the difference in refractive index between the sample solution and the solvent.

As the first step for measuring the refractive index, the first chamber 51 and the second chamber 52 are filled with the same solvent, and the slit image formed by the slit plate 4 is detected by the photosensor 8. As the second step, for example the first chamber 51 is filled with the sample solution and the second chamber 52 is filled with the solvent and the similar measurement is carried out. The positions of the slit images formed at the first and second steps, are different from each other correspondingly to the amount of deflection of the light flux A which is produced according to the difference in refractive index between the sample solution and the solvent.

The difference in refractive index $\Delta n$ is expressed according to the following equation (1):

$$\Delta n = n_S - n_R \approx \frac{e \cdot (\pm \sin \alpha)}{\tan \theta} \qquad (1)$$

where
$n_S$: Refractive index of the sample solution
$n_R$: Refractive index of the solvent
$e$: Refractive index outside of the cell
$\alpha$: Deflection angle of the light flux A
$\theta$: Angle formed between the light flux A and the partitioning plate $5b$ In the equation (1), either positive or negative sign is selected according to the refractive indexes $n_S$, $n_R$ and the angle $\theta$. On the other hand, when the distance between the cell 5 and the photosensor 8 is defined as $l$ and the variation of slit image forming position $\Delta X$ is used, $\sin \alpha$ is expressed according to the following equation (2):

$$\sin \alpha = \frac{\Delta X}{l} \qquad (2)$$

Accordingly, the equation (1) is transformed to the following equation (3):

$$\Delta n \approx \frac{e \cdot (\pm \Delta X)}{l \cdot \tan \theta} \qquad (3)$$

Since $e$ is approximately equal to 1 in the air, the difference in refractive index $\Delta n$ is finally expressed by the following equation (4):

$$\Delta n \approx \frac{\Delta X}{l \cdot \tan \theta} \qquad (4)$$

More specifically, when the displacement $\Delta X$ is known, the difference in refractive index $\Delta n$ may be obtained. Accordingly, the refractive index of the sample solution may be obtained based on the refractive index of the solvent.

FIG. 23 is a plan view illustrating the operation of the correction glass plate 7. When the dial 9 is operated to angularly displace the correction glass plate 7 by an angle $\beta$ from a reference position $7a$ (shown by a broken line in FIG. 23), the incident angle of the light flux A upon the correction glass plate 7 is equal to the angle $\beta$. In this state, when it is presumed that the light flux A is refracted so that the optical path thereof is shifted by $\Delta xa$, such a displacement of the optical path $\Delta xa$ is approximately proportional to $\sin \beta$ as follows:

$$xa \propto \sin \beta \dots \qquad (5)$$

To measure the difference in refractive index $\Delta n$, with the correction glass plate 7 assuming a posture of the reference position $7a$, the both chambers 51, 52 of the cell 5 are first filled with the solvent and the light flux A is detected by the photosensor 8. Then, the first chamber 51 of the cell 5 is filled with the sample solution and the dial 9 is operated such that the deflected light flux A is detected by the photosensor 8. In this state, the displacement $\Delta xa$ of the optical path of the light flux A by the correction glass plate 7 is expressed by the following formula (6):

$$\Delta xa \propto \Delta x \quad (6)$$

The displacement $\Delta xa$ may be obtained from the value of the dial 9. Accordingly, based on the value of the dial 9, the difference in refractive index between the sample solution and the solvent $\Delta n$ may be obtained with the use of the equation (4).

Such an arrangement, however, involves the likelihood that there is a individual difference among the operators when the dial 9 is manually operated to shift the slit image forming position. This lowers the reproducibility of data, resulting in deterioration of precision in measurement of refractive index.

Further, there is a certain time interval between the detection of a slit image formed at the time when both the chambers of the cell 5 is filled with the solvent and the detection of a slit image formed at the time when the first chamber 51 of the cell 5 is filled with the sample solution. This involves error factors such as variations of the mechanical vibration and air fluctuation with the passage of time, the deflection of an optical base (not shown) with the passage of time, and the like. This further deteriorates the measuring precision.

Other prior art is disclosed by, for example, JP-A-188744/1988 of which basic arrangement is shown in FIG. 24. Light from a light source 11 is condensed at a condensing lens 12, spatially filtered by a slit plate 13 and collimated by a collimater lens 14. The resultant parallel light portions are incident upon a V-block 15 made of a transparent material of which refractive index is known. The V-block 15 has a V-shape concave 15a having a vertical angle of 90°. The concave 15a serves as a sample stand. Placed on the concave 15a is a sample 16 which has a vertical angle of, for example, 90° and of which refractive index is unknown. Almost a half of the parallel light portions from the collimater lens 14 passes through the sample 16.

The light portions from the V-block 15 pass through a chopper 17 and are condensed by an image forming lens 18. The slit image formed by a slit plate 13 is then formed on the light receiving surface of a one-dimensional image sensor 19 formed by a one-dimensional CCD (charge coupled device) or the like. The chopper 17 has a stationary piece 17a and a movable piece 17b. The stationary piece 17a includes an opening for receiving the light portion which has passed through the sample 16 and an opening for receiving the light portion which has not passed through the sample 16. The movable piece 17b closes either one of these two openings.

To measure the refractive index of the sample 16, the light portion which has passed through the sample 16 is first intercepted by the chopper 17. The slit image forming position in this state is detected by the one-dimensional image sensor 19 and held by, for example, control means (not shown). In this case, the light portion passing through the chopper 17 is the light portion which has passed through only the V-block 15 of which refractive index is uniform, so that this light portion is not deflected.

Then, the chopper 17 intercepts, out of the light portions from the V-block 15, the light portion which has not passed through the sample 16. Thus, incident upon the image forming lens 18 is the light portion which has been deflected correspondingly to the difference in refractive index between the V-block 15 and the sample 16. This causes the slit image to be formed on a position different from the position above-mentioned, such a positional difference corresponding to the difference in refractive index. This image position is detected by the one-dimensional image sensor 19 and supplied to the control means above-mentioned. Calculated in the control means is the distance between two positions at which the slit images are respectively formed by the light portion having passed through the sample 16 and the light portion not having passed therethrough. From the result of this calculation, the difference in refractive index between the sample 16 and the V-block 15 is obtained in the same manner as in the first prior art shown in FIG. 21.

In the prior art shown in FIG. 24, the amount of light deflection is measured based on an output from the one-dimensional image sensor 19 with no manual operation required. This not only facilitates the measurement of refractive index, but also contains no measuring errors due to the individual difference among the operators, thereby to improve the measuring precision.

However, when the movable piece 17b of the chopper 17 is driven, vibration is produced to displace the slit image forming position on the one-dimensional image sensor 19. This results in deterioration of the measuring precision. Further, the incorporation of the mechanically driven member inevitably increases the number of component elements.

SUMMARY OF THE INVENTION

It is an object of the present invention to provide a differential refractometer of which measuring precision is greatly improved.

It is another object of the present invention to provide a differential refractometer in which the number of component elements is reduced, thus contributing to cost reduction.

To achieve the objects above-mentioned, the differential refractometer in accordance with the present invention comprises: a light source; a light permeable member carrying an image having at least two identification portions; a lens for condensing light from the light source through the light permeable member; an image sensor disposed at such a position that the image sensor and the light permeable member are optically conjugate with respect to the lens; a cell disposed between the light permeable member and the image sensor and housing a sample of which refractive index to be measured and a reference of which refractive index is used as a reference value, the sample and the reference being housed as separated from each other in the cell; and a spatial filter disposed between the light permeable member and the image sensor for spatially filtering light portions which have passed through the two identification portions of the light permeable member, the spatial filter causing at least one of the light portions thus spatially filtered to pass through the cell.

According to the arrangement above-mentioned, the light portion which has passed through one of at least two identification portions carried on the light permeable member, passes through the cell and forms an image at one position on the detecting surface of the image sensor. The light portion which has passed through the other identification portion, passes through the inside or outside of the cell and forms an image at another position on the detecting surface of the image sensor. These light portions are simultaneously detected in the image sensor. From the outputs of the image sensor, there may be obtained the distance between the positions of images formed by the light portions having respectively passed through the identification portions. The distance between the image forming positions corresponds to the deflection amount of the light portion having passed through the cell, such a deflection amount corresponding to the difference in refractive index between the sample and the reference. Accordingly, the difference in refractive index between the sample and the reference may be obtained based on the outputs of the image sensor.

The arrangement of the present invention contains no elements to be mechanically driven and is therefore free from mechanical vibration. This not only assures the measurement of refractive index with high precision, but also reduces the number of elements, thus contributing to cost reduction.

Further, the light portions having passed through the two identification portions are simultaneously detected by the image sensor. Accordingly, even though the position of the image formed by one light portion is shifted due to vibration, air fluctuation or the like, the position of the image formed by the other light portion also undergoes a similar change. Thus, the influences of vibration and the like exerted upon the respective image forming positions may be cancelled by obtaining the distance between the positions of the images formed by the light portions having passed through the identification portions. Accordingly, the distance between the image forming positions may be detected with high precision to improve the precision in measurement of refractive index.

Further, since the light permeable member and the image sensor are so disposed as to be optically conjugate with respect to the lens, the images of the light permeable member may be clearly formed on the detecting surface of the image sensor. The spatial filter may separate definitely, from each other, the light portions having passed through the two identification portions of the image carried on the light permeable member. This enables one of the separated light portions to pass definitely through one optical path in the cell, e.g., the optical path passing through either the sample or the reference (or the optical path outside of the cell), and also enables the other light portion to pass definitely through the other optical path in the cell, e.g., the optical path which inclinedly passes through the interface of the sample and the reference. Thus, the light portions having respectively passed through the two identification portions may be separated definitely from each other on the detecting surface of the image sensor. It is therefore possible to improve the precision in measurement of the distance between the positions of the images formed by the light portions having passed through the identification portions.

The features above-mentioned of the present invention will be more apparent from the following description with reference to the attached drawings.

DESCRIPTION OF THE PREFERRED EMBODIMENTS

Figure 1:
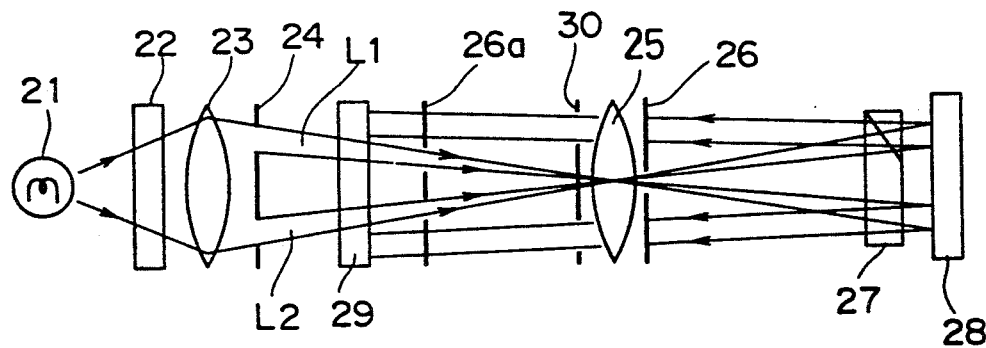
FIG. 1 is a schematic plan view of the basic arrangement of a differential refractometer in accordance with an embodiment of the present invention.
Figure 2:
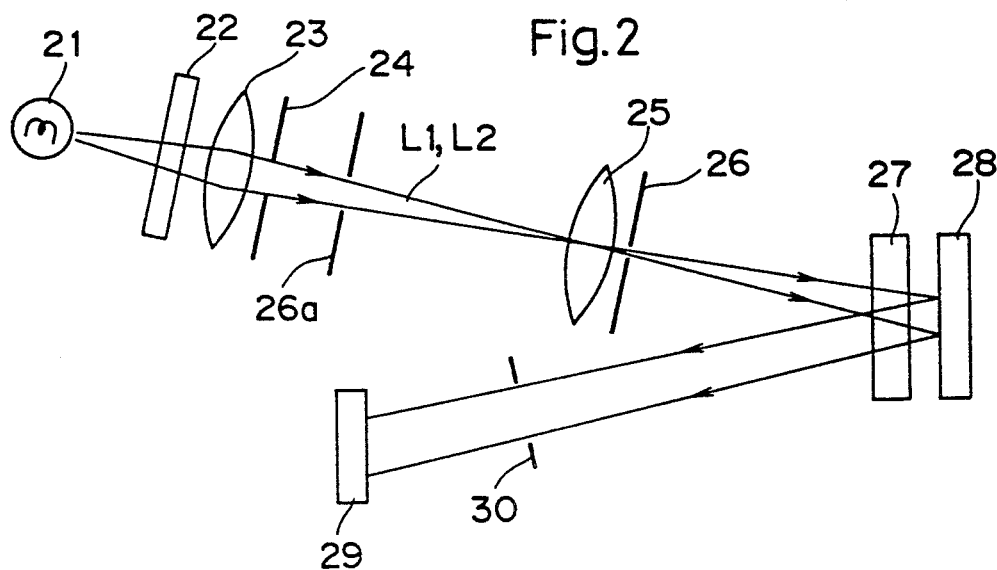
FIG. 2 is a front view of the arrangement shown in FIG. 1.
Figure 3:
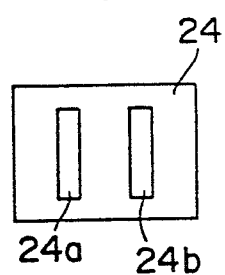
FIG. 3 is a front view of a slit plate 24.

FIG. 1 is a schematic plan view illustrating the basic arrangement of a differential refractometer in accordance with an embodiment of the present invention, while FIG. 2 is a front view thereof. Light from a light source 21 passes through an interference filter 22 and is guided to a condensing lens 23 where the light is condensed. The condensed light passes through a slit plate 24 having two slender openings 24a, 24b as shown in FIG. 3, thereby to form light fluxes L1, L2. In this embodiment, the slit plate 24 serves as a light permeable member.

Through an image forming lens 25, the light fluxes L1, L2 from the slit plate 24 are incident upon a cell 27 through an aperture 26 such as a pinhole formed on the optical axis of the image forming lens 25. The aperture 26 serves as a spatial filter. The light fluxes L1, L2 having passed through the cell 27 are reflected by a reflector 28 and again pass through the cell 27. Then, the light fluxes L1, L2 form images corresponding to the openings 24a, 24b of the slit plate 24 on the one-dimensional image sensor 29. The slit plate 24 and the one-dimensional image sensor 29 are so disposed as to be optically conjugate with respect to the image forming lens 25. Accordingly, the images of the openings 24a, 24b of the slit plate 24 are clearly formed on the detecting surface of the one-dimensional image sensor 29. A light cutting plate 30 prevents ambient excessive light portions from being incident upon the one-dimensional image sensor 29.

Figure 4:
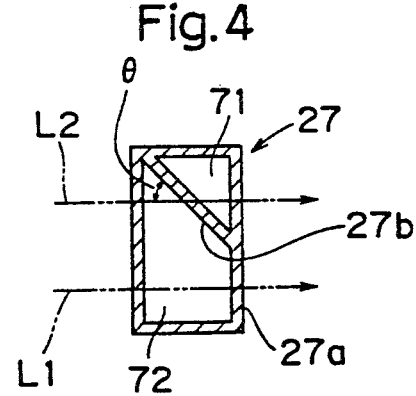
FIG. 4 is a section view of a cell 27.

FIG. 4 is a transverse section view of the cell 27. This cell 27 is made of a transparent casing body having a rectangular section. The inside space thereof is obliquely partitioned by a transparent partitioning plate 27b to form a first chamber 71 and a second chamber 72. For example, the first chamber 71 is filled with a sample such as a sample solution of which refractive index is to be measured, while the second chamber 72 is filled with a reference such as a solvent for the sample.

After having passed through the second chamber 72 and the partitioning plate 27b, the light flux L2 advances toward the reflector 28 through the first chamber 71, while the light flux L1 passes through the second chamber 72 only. After having been reflected by the reflector 28, the light fluxes L1, L2 advance in the direction substantially opposite to that shown in FIG. 4. Thus, the light flux L2 which has passed through both the sample solution in the first chamber 71 and the solvent in the second chamber 72, is deflected correspondingly to the difference in refractive index between the sample solution and the solvent. On the other hand, the light flux L1 which has passed through the solvent only, is not deflected due to the difference in refractive index. Accordingly, the distance between the positions of the images of the openings 24a, 24b in the slit plate 24 detected by the one-dimensional image sensor 29, corresponds to the difference in refractive index between the sample solution and the solvent. The foregoing is also applied to the case where the first chamber 71 is filled with the solvent, while the second chamber 72 is filled with the sample solution. More specifically, the light flux L2 which has passed through the partitioning plate 27b, is deflected correspondingly to the difference in refractive index, while the light flux L1 which has passed through the second chamber 72 only, is not deflected correspondingly to the difference in refractive index.

The aperture 26 disposed at the back side of the image forming lens 25 sufficiently spatially filters the light fluxes L1, L2 such that the light flux L2 passes definitely through the partitioning plate 27b of the cell 27 and that the light flux L1 passes definitely through only the second chamber 72 of the cell 27. It is therefore possible that the light flux L2 having passed through both the sample solution and the solvent and the light flux L1 having passed through the solvent only, are separated definitely from each other and respectively form images on the detecting surface of the one-dimensional image sensor 29.

Figure 5:
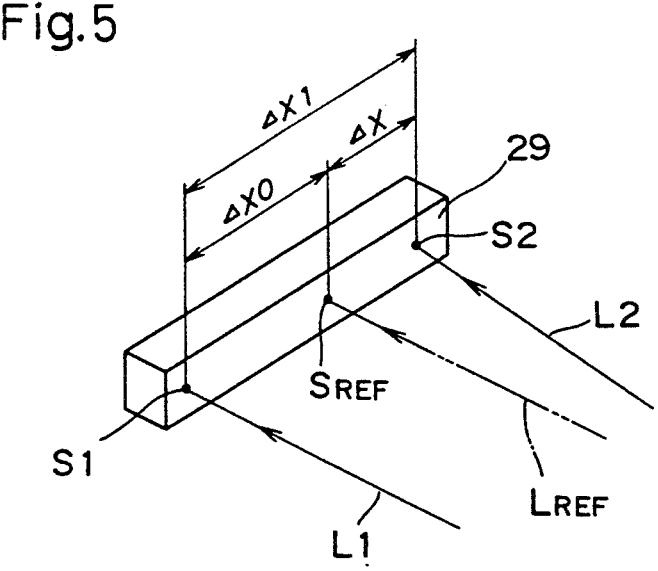
FIG. 5 is a perspective view illustrating the principle of measurement of refractive index.

FIG. 5 is a perspective view illustrating the principle of measurement. FIG. 5 shows how the light fluxes L1, L2 form images on the detecting surface of the one-dimensional image sensor 29. When both the first chamber 71 and the second chamber 72 of the cell 27 are filled with the solvent for the sample solution, the light flux L2 is incident, as not deflected, upon the detecting surface of the one-dimensional image sensor 29 through an optical path $L_{REF}$. The positional shift $\Delta X$ between the position $S_{REF}$ of the image of the light flux L2 as not deflected and the position S2 of the image of the light flux L2 as deflected when the first chamber 71 is filled with the sample solution, corresponds to the difference in refractive index between the sample solution and the solvent. It is the difference $\Delta X1$ between the image forming position S1 of the light flux L1 and the image forming position S2 of the light flux L2 that is detected by the one-dimensional image sensor 29. However, when the distance $\Delta X0$ between the image forming positions S1 and $S_{REF}$ is previously obtained, the positional shift $\Delta X$ (= $\Delta X1 - \Delta X0$) may be obtained.

In the embodiment above-mentioned, the optical paths of the light fluxes L1, L2 are turned back by the reflector 28. Accordingly, the light fluxes L1, L2 pass through the cell 27 twice and, therefore, the light flux L2 is deflected twice. In this connection, the positional shift $\Delta X$ corresponds to a value twice the value of displacement of the slit image in the conventional arrangement shown in each of FIGS. 21 and 24. According to the differential refractometer of this embodiment, the difference in refractive index $\Delta n$ may be obtained by replacing $\Delta x$ in the equation (3) above-mentioned by $\Delta X/2$, and finally calculated according to the following equation (7):

$$\Delta n \approx \frac{e \cdot (\pm \Delta X/2)}{l \cdot \tan\theta} \quad (7)$$
$$= \frac{e \cdot (\pm \Delta X)}{2 \cdot l \cdot \tan\theta}$$

where
  $\theta$: Angle formed between the light flux L2 and the partitioning plate 27b of the cell 27 (See FIG. 4),
  l: Distance between the cell 27 and the detecting surface of the one-dimensional image sensor 29

When the distance between elements, such as photodiodes (not shown), of the one-dimensional image sensor 29 is assumed to be $56 \times 10^{-3}$ (mm), $\Delta X$ may be expressed, with the use of the number m of the elements which are present between the slit image forming positions, by the following equation (8):

$$\Delta X = m \times (56 \times 10^{-3}) \dots \quad (8)$$

Accordingly, the equation (7) may be transformed into the following equation (9):

$$\Delta n = \frac{e}{2 \cdot l \cdot \tan\theta} (\pm 56 \times 10^{-3}) \cdot m \quad (9)$$

Figure 6:
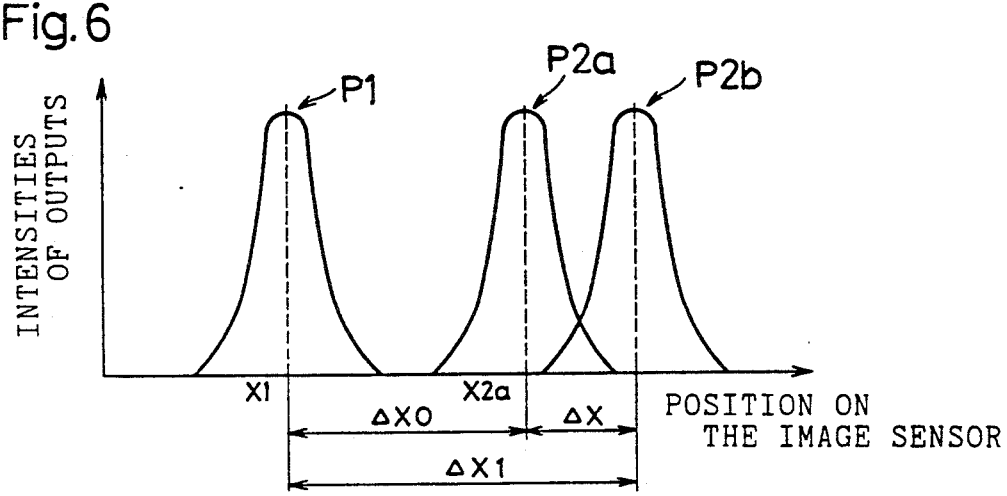
FIG. 6 is a view illustrating the intensities of outputs from a one-dimensional image sensor 29.

FIG. 6 is a view illustrating the intensities of output signals from the one-dimensional image sensor 29. In FIG. 6, the abscissa axis represents one-directional coordinates selected in the aligning direction of the elements of the one-dimensional image sensor 29, while the ordinate axis represents the intensity of an output signal. In FIG. 6, a peak P1 corresponds to the light flux L1, a peak P2a corresponds to the light flux L2 in the state where the first chamber 71 is filled with the solvent, and a peak P2b corresponds to the light flux L2 in the state where the first chamber 71 is filled with the sample solution. In FIG. 5, the distance $\Delta X1$ corresponds to the distance between the top points of the peaks P1, P2b, the distance $\Delta X0$ corresponds to the distance between the top points of the peaks P1, P2a, and the positional shift $\Delta X$ corresponds to the distance between the top points of the peaks P2a, P2b. These distances are also shown in FIG. 6.

Since the light flux L1 forming the peak P1, for example, is sufficiently spatially filtered under the action of the aperture 26, the peak P1 may have a sufficiently pointed shape. This is also applied to the peaks P2a, P2b.

When determining the peak positions in this embodiment, there are calculated the areas of portions surrounded by the peaks and the coordinate axis (hereinafter referred to as peak areas). The coordinate values at which the peak areas are divided into two equal parts, are determined as the peak positions. Such a peak position determining method makes it possible to determine the peak positions more minutely than the distance between the neighboring elements in the one-dimensional image sensor 29.

To determine the peak positions, there may be alternately applied a method by which the amount of light $I_i$ detected by each element of the one-dimensional image sensor 29 is used as weight, and the average position $x_M$ is calculated according to the following equation (10), and the average position $x_M$ thus calculated is used as a peak position:

$$x_M = \frac{\Sigma I_i \cdot X}{\Sigma I_i} \qquad (10)$$

where x: Coordinate positions on the detecting surface of the one-dimensional image sensor 29.

However, this method presents the disadvantage that data deviating from the average position $x_M$ are overemphasized. According to the method above-mentioned by which the coordinate position dividing each peak area into two equal parts is determined as each peak position, the importance of all the light is made uniform and almost all the received light is handled as effective data. Thus, this method presents the advantage to enhance the precision of peak positions.

To determine the peak positions, there may be also used, for example, technique disclosed in JP-A-295935/1988. According to this technique disclosed in the laid-open publication, when light is received by, for example, five elements in the one-dimensional image sensor, the center of gravity of a pentagon formed on a graph which shows the relationship between the amounts of light and the coordinate positions is determined as the peak position. Then, there is determined, as the peak height, the height of a triangle having a predetermined base of which area is equal to the area of the pentagon. Accordingly, even though the peak intensity position of light incident upon the image sensor is located in a non-photoelectric transformation area, the peak position and height are accurately detected. This method may also make it possible to determine the peak positions more minutely than the distance between the neighboring elements.

Figure 7:
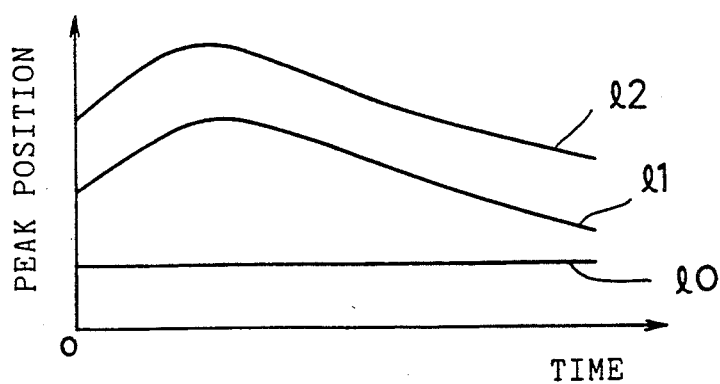
FIG. 7 is a view illustrating variations, with the passage of time, of the positions of coordinates of peaks P1, P2a in FIG. 6.
Figure 8:
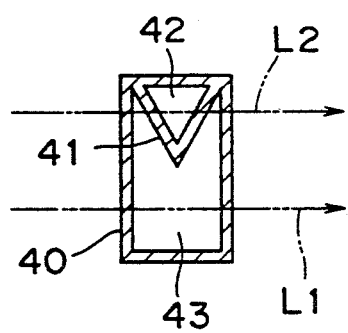
FIGS. 8 to 12 are section views of examples of an applicable cell.
Figure 9:
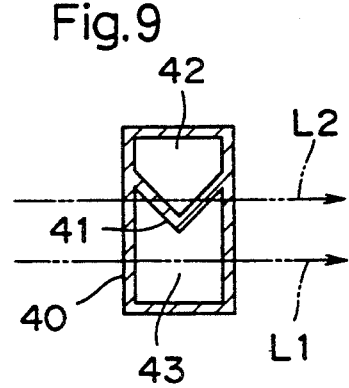
Figure 10:
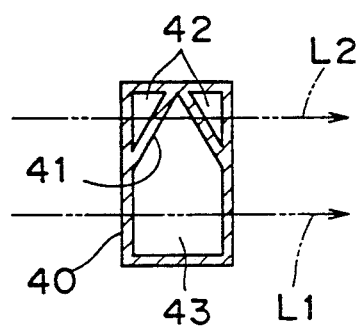
Figure 11:
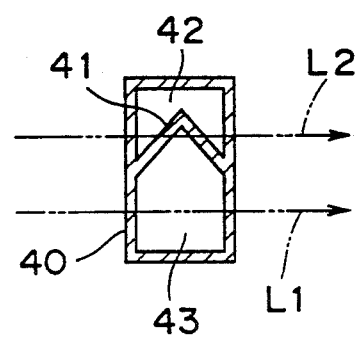

FIG. 7 shows variations, with the passage of time, of the peak position coordinates x1 of the peak P1 corresponding to the light flux L1 (See FIG. 6) and the peak position coordinates x2a of the peak P2a corresponding to the light flux L2 in the state where the first chamber 71 is filled with the solvent (See FIG. 6). The image forming positions of the light fluxes L1, L2 are influenced by mechanical vibration, air fluctuation or the like and vary with the passage of time as respectively shown by curves 11, 12. Such variations of the image forming positions appear equally on the light fluxes L1, L2. Accordingly, the distance $\Delta X0$ between the image forming positions of the light fluxes L1, L2 undergoes no substantial change with the passage of time as shown by a curve 10. The test conducted by the inventors of the present invention revealed that the variation of the distance $\Delta X0$ with the passage of time is only $(\pm 2/1000) \times 56 \times 10^{-3}$ (mm).

Thus, the distance $\Delta X0$ may be accurately measured with the influence of mechanical vibration and the like excluded. The foregoing may also be applied to the case where the first chamber 71 of the cell 27 is filled with the sample solution. Accordingly, the distance $\Delta X1$ in FIG. 5 may be accurately measured. As a result, the positional shift $\Delta X$ may be obtained with high precision. More specifically, this embodiment is so arranged as to simultaneously detect the light flux L2 having passed through the sample solution and the light flux L1 having passed through only the solvent. Thus, the influence of mechanical vibration, air fluctuation or the like appears commonly on the light fluxes L1, L2 in the form of variations of the image forming positions thereof. Accordingly, the distances between the image forming positions may be accurately measured with such error factors as above-mentioned cancelled.

For example, when the distance 1 between the cell 27 and the one-dimensional image sensor 29 is supposed to be 300 (mm) and the angle $\theta$ is supposed to be 45°, the minimum sensitivity to be detected $\Delta n_{min}$ is expressed by the following equation (11):

$$\Delta n_{min} = \frac{(\pm 2/1000) \times 56 \times 10^{-3}}{2 \times 300 \times 1} \qquad (11)$$

$$= 1.9 \times 10^{-7}$$

As described in the foregoing, the influence of mechanical vibration or the like is minimized so that the sensitivity to be detected expressed by the equation (11) may be readily obtained.

Figure 21:
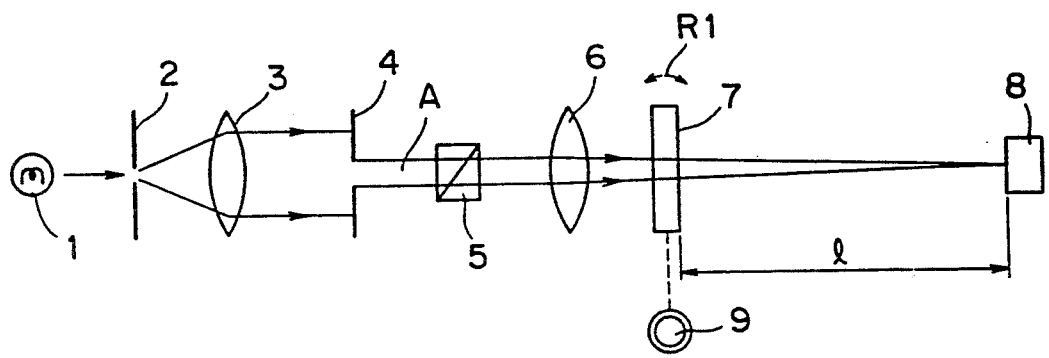
FIG. 21 is a schematic plan view of the arrangement of a first conventional differential refractometer.
Figure 24:
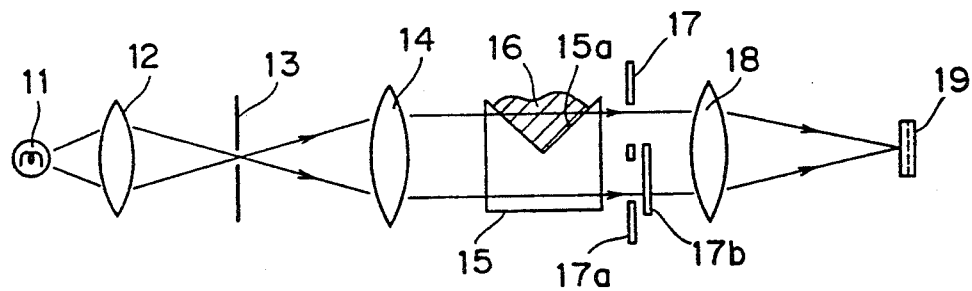
FIG. 24 is a schematic front view of the arrangement of a second conventional differential refractometer.

As thus described, the arrangement of this embodiment does not incorporate such a mechanically driven member as the correction glass plate 7 in the first prior art shown in FIG. 21 or as the chopper 17 in the second prior art shown in FIG. 24. That is, the respective component elements are always stationary during measurement. This not only prevents the occurrence of undesired mechanical vibration, but also reduces the number of the component elements, thereby to be advantageous in view of cost reduction. Further, the positional shift $\Delta X$ of the image forming position of the light flux L2 may be measured with high precision with no influence of mechanical vibration, variations of the optical base (not shown) with the passage of time, or the like, thus enabling the refractive index to be measured with very high precision.

Further, two light fluxes L1, L2 are formed from the light from the single light source 21 and then spatially filtered by aperture 26, causing the light fluxes L1, L2 to be incident, in the form of definitely separated beams, upon the cell 27. This assures that the light flux L2 passes through both the sample solution and the solvent and the light flux L1 passes through the solvent only. Further, the slit plate 24 for forming the light fluxes L1, L2 from the light from the light source, is disposed at such a position that the slit plate 24 and the one-dimensional image sensor 29 are optically conjugate with respect to the image forming lens 25. Accordingly, the images of the openings 24a, 24b in the slit plate 24 are clearly formed on the detecting surface of the one-dimensional image sensor 29. These two factors abovementioned make it possible to measure, with much higher precision, the distance $\Delta X1$ between the positions of the images of the openings 24a, 24b in the slit plate 24 by the one-dimensional image sensor 29.

As the cell which houses a sample and a reference as separated from each other, there may be used any of cells having arrangements respectively shown in FIGS. 8 to 11, instead of the cell 27 in FIG. 4. In each of the cells in FIGS. 8 to 11, a cell container 40 is formed by a transparent casing body having a rectangular section, and the inside space of the cell container 40 is partitioned by a transparent partitioning plate 41 having a V-shape section. For example, a sample of which refractive index is to be measured is placed in one chamber 42, while a reference of which refractive index is known, is placed in the other chamber 43. When such a cell is used, provision may be made such that the light flux L2 passes through the partitioning plate 41. In this case, when the light flux L2 passes through the cell once, the light flux L2 is deflected twice correspondingly to the difference in refractive index between the sample and the reference. Accordingly, the amount of deflection is doubled as compared with the case using the cell 27 shown in FIG. 4. This may further improve the precision in measurement of refractive index.

Figure 12:
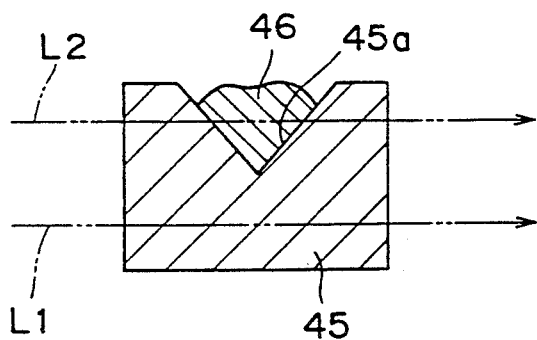

FIG. 12 shows an example of an applicable cell. This cell uses a V-shape block 45 having a V-shape concave 45a made of a transparent solid material of which refractive index is known. A solid or liquid sample 46 of which refractive index is to be measured, is to be placed or housed in the concave 45a of the V-block 45. In this cell, the V-block 45 serves as a reference.

In addition to the cells above-mentioned, there may be also used a cell arranged such that, when two light fluxes are simultaneously incident upon the cell, one light flux passes through both a sample and a reference, while the other light flux passes through either the sample or the reference only.

There may be also used a cell arranged such that both light fluxes pass through both a sample and a reference. In this case, however, it is required that the angles respectively formed by the two light fluxes and a partitioning plate which partitions the sample and the reference from each other, are different from each other such that the light fluxes after deflected, are not in parallel in the advancing directions thereof.

Further, the sample and the reference are not necessarily a fluid such as a liquid, but may be a solid.

Figure 13:
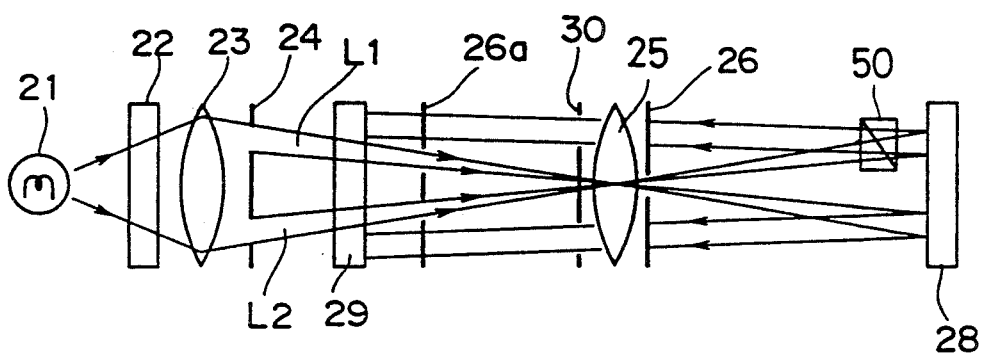
FIG. 13 is a schematic plan view of the basic arrangement of a differential refractometer in accordance with another embodiment of the present invention.
Figure 14:
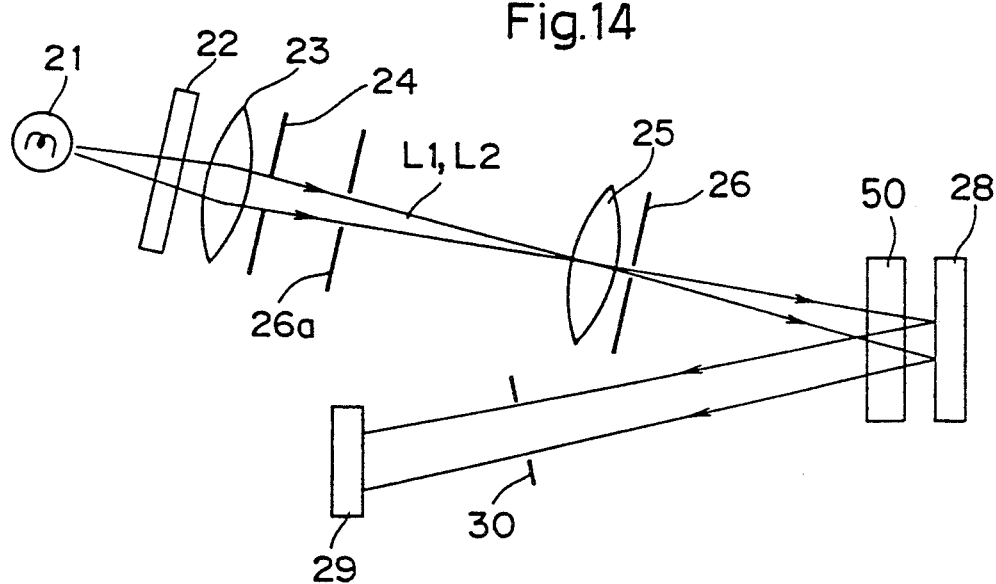
FIG. 14 is a front view of the arrangement shown in FIG. 13.

FIG. 13 is a schematic plan view showing a basic arrangement of a differential refractometer in accordance with another embodiment of the present invention, while FIG. 14 is a front view of FIG. 13. In FIGS. 13 and 14. the parts corresponding to those shown in FIGS. 1 and 2 are designated by the same reference numerals used therein.

Figure 22:
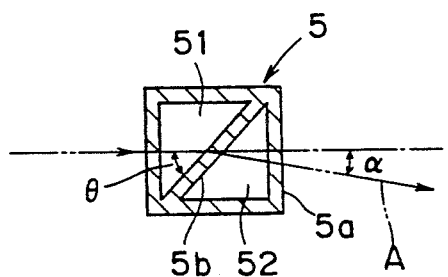
FIG. 22 is a section view of a cell 5.
Figure 23:
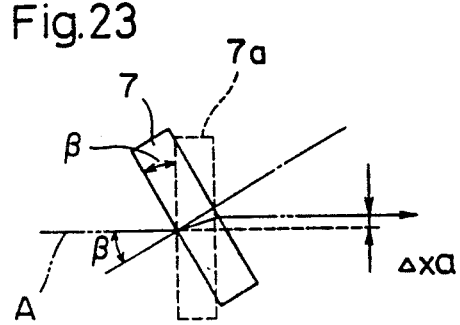
FIG. 23 is a plan view illustrating the operation of a correction glass plate 7.

In the embodiment shown in FIGS. 13 and 14, a cell 50 similar to the Brice cell in FIG. 22 is used instead of the cell 27 in FIGS. 1 and 2. The light flux L2 passes through the cell 50, while the light flux L1 is propagated in the air outside of the cell 50. The inside space of the cell 50 is partitioned into two chambers by a partitioning plate disposed inclinedly with respect to the light flux L2. A sample of which refractive index is to be measured is housed in one chamber of the cell, while a reference of which refractive index is known is housed in the other chamber. This reference may be air.

According to the arrangement above-mentioned, the light flux L2 is deflected correspondingly to the difference in refractive index between the sample and the reference. On the other hand, the light flux L1 is not deflected due to the difference in refractive index. Accordingly, the distance between the image forming positions of the light fluxes L1, L2 detected by the one-dimensional image sensor 29, corresponds to the difference in refractive index. Thus, this embodiment may achieve operational effects similar to those achieved in the embodiment shown in FIGS. 1 and 2.

Figure 15:
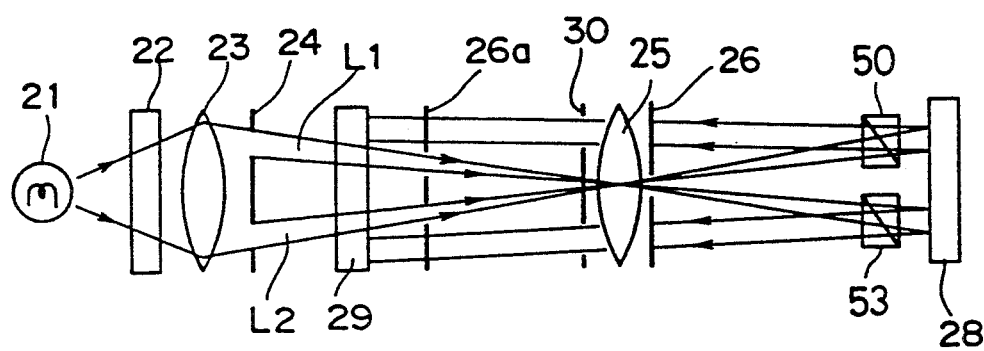
FIG. 15 is a schematic plan view of the basic arrangement of a differential refractometer in accordance with a further embodiment of the present invention.

Alternately, as shown in FIG. 15, there may be disposed, in the optical path of the light flux L1 passing through the outside of the cell 50, an empty cell 53 which has an arrangement similar to that of the cell 50 and which houses air in both chambers thereof. In this case, the influence of the cell 50 exerted upon the light flux L2 may be cancelled by detecting the distance between the image forming positions of the light fluxes L1, L2 by the one dimensional image sensor 29. This may further improve the precision in measurement of refractive index. Alternately, there may be used a solid cell made of a transparent solid material, instead of the empty cell 53.

As the cell 50, there may be alternately used a cell including a partitioning plate having a V-shape section, which is similar to any of the cells in FIGS. 8 to 11, or a cell as shown in FIG. 12. With the use of such a cell, the light flux L2 is adapted to be deflected twice when the light flux L2 passes once through the cell. This may further improve the precision in measurement of refractive index.

Figure 16:
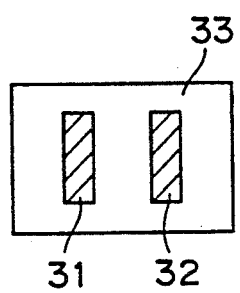
FIGS. 16 to 20 are front views of examples of an applicable light permeable member.
Figure 17:
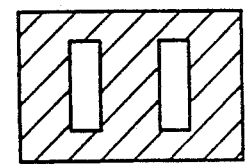

In each of the embodiments above-mentioned, the slit plate 24 is so arranged as to form two light fluxes L1, L2 as separated from each other. Instead of the slit plate 24, there may be alternately used a light permeable member carrying an image which has at least two identification portions. More specifically, the light permeable member may be formed, for example, such that a transparent plate-like member 33 has, as shown in FIG. 16, at least two light intercepting portions 31, 32 (hatched portions in FIG. 16) which are being formed in pattern, and that these light intercepting portions 31, 32 serve as the identification portions. Alternately, the light permeable member may be formed, as shown in FIG. 17, reversely of the light permeable member in FIG. 16 with respect to the arrangement of the light intercepting portions and the light permeable portions.

Figure 18:
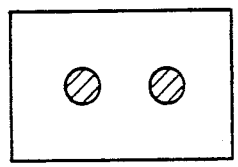
Figure 19:
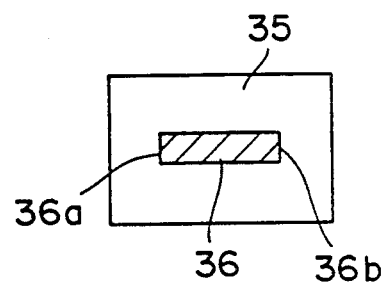
Figure 20:
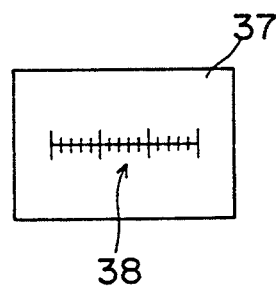

Each of the light intercepting portions may have any shape, which may be circular as shown in FIG. 18. There may be also used a light permeable member as shown in FIG. 19 in which a transparent plate-like member 35 has a rectangular light intercepting portion 36 of which both ends 36a, 36b, for example, serve as the two identification portions. There may be also used a light permeable member as shown in FIG. 20 in which a transparent plate-like member 37 has a scale 38 on the surface thereof. Thus, when there is used a light permeable member carrying an image which has at least two identification portions, it is possible to obtain, based on an detection output from the one-dimensional image sensor 29, the amount of deflection of the light which has passed through the sample and the reference.

In each of the embodiments above-mentioned, there is used, as the spatial filter, the aperture 26 which has a pinhole on the optical axis of the image forming lens 25 and which is disposed in the vicinity of the backside of the image forming lens 25. However, the shape and position of the spatial filter are not limited to those in each of the embodiments above-mentioned. The spatial filter may be shaped and positioned such that the light portions incident upon the one-dimensional image sensor 29 are definitely divided into the light portion which has passed through the partitioning plate 27b of the cell 27 and the light portion which has not passed therethrough. More specifically, in each of the arrangements in FIGS. 1, 2, FIGS. 13, 14 and FIG. 15, there may be disposed, instead of the aperture 26, a spatial filter having one or two pinholes, at an arbitrary position between the slit plate 24 and the one-dimensional image sensor 29. That is, the spatial filter 26a formed by a plate-like member having two pinholes as shown in FIG. 1, FIG. 13 or FIG. 15, may be disposed, instead of the aperture 26, between the condensing lens 23 and the image forming lens 25. The number of such spatial filters is not limited to one, but a plurality of such spatial filters may be disposed in the optical paths from the slit plate 24 to the one-dimensional image sensor 29.

The light cutting plate 30 may be disposed, for example, between the aperture 26 and the cell 27, or between the cell 27 and the reflector 28. A plurality of light cutting plates may also be used.

In each of the embodiments above-mentioned, the optical paths of the light fluxes L1, L2 are turned back with the use of the reflector 28. This not only makes the entire arrangement in a compact design, but also causes each light flux L1 or L2 to pass through the cell 27 twice to increase the deflection amount of the light flux L2, thus improving the measuring precision. However, the reflector 28 is not necessarily required. There may be adopted a linear arrangement in which the one-dimensional image sensor 29 is disposed backside of the cell 27 without use of the reflector 28, so that each light flux L1 or L2 passes through the cell 27 one time.

It should be understood that various modifications of the present invention may be made without departing from the scope thereof.

What we claim is:

1. A differential refractometer comprising:
   a light permeable member working as an apparent light source and carrying an image having at least two identification portions;
   a light source for illuminating said light permeable member;
   a lens for condensing light from said light source which has passed through said light permeable member;
   an image sensor disposed at such a position that said image sensor and said light permeable member are optically conjugate with respect to said lens, so that the image of said light permeable member may be clearly formed on the detecting surface thereof;
   a cell disposed between said light permeable member and said image sensor and housing a sample of which refractive index to be measured and a reference of which refractive index is used as a reference value, said sample and said reference being housed as separated from each other in said cell, said cell having a predetermined measuring area where an incident light passes through both said sample and said reference; and
   a spatial filter disposed between said light permeable member and said image sensor for spatially filtering light portions which have passed through said two identification portions of said light permeable member, in order to make clear the image of said light permeable member formed on the detecting surface of said image sensor, and said spatial filter causing one of said light portions thus spatially filtered to pass through only said predetermined measuring area of said cell and the other of said light portions thus spatially filtered not to pass through said predetermined measuring area of said cell.

2. A differential refractometer according to claim 1, wherein:
   the light portion having passed through one of the two identification portions, passes through both the sample and the reference housed in the cell; and
   the light portion having passed through the other identification portion, passes through the outside of said cell.

3. A differential refractometer according to claim 2, wherein the light portion to pass through the outside of the cell, is propagated in the air.

4. A differential refractometer according to claim 2, wherein an empty cell housing air is interposed in the optical path of the light portion to pass through the outside of the cell.

5. A differential refractometer according to claim 2, wherein a solid cell made of a transparent solid material is interposed in the optical path of the light portion to pass through the outside of the cell.

6. A differential refractometer according to claim 2, wherein the cell is a Brice cell.

7. A differential refractometer according to claim 1, wherein the spatial filter is adapted to spatially filter the light portions having passed through the two identification portions into a light portion adapted to pass through one of the sample and the reference in the cell, and a light portion adapted to pass through both said sample and said reference in said cell, causing said light portion to be deflected correspondingly to the difference in refractive index between said sample and said reference.

8. A differential refractometer according to claim 7, wherein
   the cell has a partitioning plate so disposed as to be substantially vertical to the plane containing both the optical path of the light portion which passes through one of the sample and the reference and the optical path of the light portion which passes through both said sample and said reference and which is deflected correspondingly to the difference in refractive index between said sample and said reference, and to be inclined with respect to said optical path of said light portion which passes through both said sample and said reference, amd
   said sample and said reference are partitioned by said partitioning plate.

9. A differential refractometer according to claim 1, wherein the cell is formed by a block body made of a transparent solid material of which refractive index is known, said block body having a concave on which a sample is to be placed.

10. A differential refractometer according to claim 1, wherein the light permeable member is a slit plate having at least two openings.

11. A differential refractometer according to claim 10, wherein the position of an image formed on the detecting surface of the image sensor by each of light portions having passed through the openings, is detected in the form of the coordinates of a position at which the area of a peak formed in a graph showing the relationship between the position on said image sensor and the intensity of an output signal therefrom is divided into two equal parts.

12. A differential refractometer according to claim 1, wherein the light permeable member is made in the form of a transparent plate-like member which has a light intercepting portion having at least two identification portions.

13. A differential refractometer according to claim 1, wherein the light permeable member is made in the form of a transparent plate-like member having a scale.

14. A differential refractometer according to claim 1, wherein a light cutting plate is disposed between the light permeable member and the image sensor for preventing unnecessary ambient light from being incident upon said image sensor.

15. A differential refractometer according to claim 1, further comprising a reflector for reflecting the light having passed through the cell via the lens, said reflector being disposed such that the light as reflected is guided to said image sensor through said cell.

* * * * *